(12) United States Patent
Pålsson

(10) Patent No.: US 11,080,985 B2
(45) Date of Patent: Aug. 3, 2021

(54) ALARM TRIGGERING DEVICE AND CIRCUITRY THEREFOR

(71) Applicant: Stylos Design AB, Malmö (SE)

(72) Inventor: Hanne Pålsson, Malmö (SE)

(73) Assignee: Stylos Design AB, Malmö (SE)

( * ) Notice: Subject to any disclaimer, the term of this patent is extended or adjusted under 35 U.S.C. 154(b) by 309 days.

(21) Appl. No.: 16/319,559

(22) PCT Filed: Jul. 22, 2016

(86) PCT No.: PCT/EP2016/067562
§ 371 (c)(1),
(2) Date: Jan. 22, 2019

(87) PCT Pub. No.: WO2018/014974
PCT Pub. Date: Jan. 25, 2018

(65) Prior Publication Data
US 2021/0090425 A1  Mar. 25, 2021

(51) Int. Cl.
*A61B 1/00* (2006.01)
*G08B 25/01* (2006.01)
*G08B 7/06* (2006.01)
*G08B 21/04* (2006.01)
*G08B 25/10* (2006.01)

(52) U.S. Cl.
CPC ............. *G08B 25/016* (2013.01); *G08B 7/06* (2013.01); *G08B 21/043* (2013.01); *G08B 21/0446* (2013.01); *G08B 25/10* (2013.01)

(58) Field of Classification Search
CPC .................................. A61B 1/00; G06Q 10/00
See application file for complete search history.

(56) References Cited

U.S. PATENT DOCUMENTS

| | | | | |
|---|---|---|---|---|
| 2010/0281490 | A1* | 11/2010 | Powell | G06Q 20/00 |
| | | | | 719/313 |
| 2012/0194976 | A1* | 8/2012 | Golko | H04M 1/04 |
| | | | | 361/679.01 |
| 2014/0027521 | A1* | 1/2014 | Pedicano | G09F 3/14 |
| | | | | 235/492 |

FOREIGN PATENT DOCUMENTS

| | | |
|---|---|---|
| DE | 102008059463 | 3/2010 |
| EP | 2955607 | 12/2015 |
| JP | H08180286 A | 7/1996 |

(Continued)

OTHER PUBLICATIONS

English tranlsation of DE-102008059463-A1 (Year: 2010).*

(Continued)

*Primary Examiner* — Shirley Lu
(74) *Attorney, Agent, or Firm* — Shami Messinger PLLC

(57) ABSTRACT

The present invention relates to an alarm triggering device. The alarm triggering device comprises a wristband (10) adapted to be worn by a user; and circuitry (30). The circuitry (30) comprises a power source (31) configured to power one or more units of the circuitry; first and second triggering buttons (32a, 32b) arranged on separate locations along an circumferential extension of the wristband allowing for simultaneous actuation by the user applying a gripping force by gripping the wristband; an alarm detection unit (33) configured to detect an alarm by detecting simultaneous actuation of the first and second triggering buttons; and a wireless communication unit (34) configured to wirelessly send an alarm message comprising the alarm to one or more alarm receiving units.

23 Claims, 2 Drawing Sheets

(56) References Cited

FOREIGN PATENT DOCUMENTS

| JP | 2003256956 A   | 9/2003  |
|----|----------------|---------|
| JP | 2005174029 A   | 6/2005  |
| JP | 2007094942 A   | 4/2007  |
| JP | 2008501159 A   | 1/2008  |
| JP | 2014107719 A   | 6/2014  |
| WO | 03088174 A1    | 10/2003 |
| WO | WO2018014974   | 8/2012  |
| WO | 2015050796 A1  | 4/2015  |
| WO | 2016103978 A1  | 6/2016  |

OTHER PUBLICATIONS

Office Action, Japanese Patent application No. 2019-524509, dated Jul. 31, 2020, 10 pages.
PCT/EP2016/067562, Applicant Palsson Hanne, International Search Report and written opinion, dated Mar. 24, 2017, 12 pages.
International Search Report and Written Opinion, filed in international application No. PCT/EP201/067562. 12 pages.

* cited by examiner

ALARM TRIGGERING DEVICE AND CIRCUITRY THEREFOR

TECHNICAL FIELD

The present invention relates to an alarm triggering device and to circuitry of the alarm triggering alarm.

BACKGROUND

An emergency alarm system makes it possible for elderly and disabled to live alone in their homes.

Emergency alarm systems of today consist of a base station located somewhere in a users home and a wristband with a triggering button. The base station is configured to communicate with one or more predetermined caretakers. The caretakers may e.g. be relatives or a help center. The wristband with the triggering button is worn by the user. The wristband with the triggering button is moreover configured to be in wireless communication with the base station. The working distance of the wireless connection between the base station and the wristband with the triggering button is typically 100-150 meters, in an obstacle free environment.

Upon emergency the user actuates the triggering button on the wristband and an alarm signal is sent to the base station. In case of being within range the base station receives the alarm signal and sends an alarm message to the one or more predetermined caretakers. Upon answering the alarm message a telephone connection between the caretaker and the base station may be established. The user and the caretaker may thereafter communicate via the telephone connection. However, a prerequisite is that the caretaker is within audible distance of the base station.

In addition to what has been discussed above, it may be troublesome for the user to actually actuate the triggering button on the wristband.

Hence, there is a need for improvements in emergency alarm systems.

SUMMARY OF THE INVENTION

In view of the above, it is an object of the present invention to provide improvements in emergency alarm systems.

According to a first aspect an alarm triggering device is provided. The alarm triggering device comprises a wristband adapted to be worn by a user; and circuitry. Wherein the circuitry comprises: a power source configured to power one or more units of the circuitry; first and second triggering buttons arranged on separate locations along an circumferential extension of the wristband allowing for simultaneous actuation by the user applying a gripping force by gripping the wristband; an alarm detection unit configured to detect an alarm by detecting simultaneous actuation of the first and second triggering buttons; and a wireless communication unit configured to upon detection of the alarm wirelessly send an alarm message to one or more alarm receiving units.

By allowing for simultaneous actuation by the user applying a gripping force by gripping the wristband simple, efficient and fail proof means for triggering the alarm is provided. Applying a gripping force is one of the easiest ways off applying a force for human beings, especially for elder and disabled persons.

The first and second triggering buttons may be configured to be actuated by overcoming a resilient force. Efficient means for actuating the first and second triggering buttons are hence provided.

The first button may be arranged opposite the second button along the circumferential extension of the wristband.

The first button may be arranged to be actuated by applying a radially inward directed force. The second button may be arranged to be actuated by applying a radially inward directed force. Especially, the first button may be arranged to be actuated by a thumb of the user gripping the alarm triggering device and the second button may be arranged to be actuated by an index finger of the user gripping the alarm triggering device.

The power source, the alarm detection unit and the wireless communication unit are comprised in an electronic module may be removably integrated with the wristband. Hence, an alarm triggering device being easier to assemble is provided. Moreover, this allow for easy recycling of the wristband and the electronic module.

The electronic module may be made of formstable polymer material, preferably thermoplastic material. By the electronic module being made of formstable polymer material the units of the electronic module are safely hold in their mutual positions so that connections between them are not being broken. Hence, a prolonged lifetime of the electronic module is provided. The use of thermoplastic material facilitates the manufacturing of the electronic module.

The wristband is made of elastic polymer material, preferably thermoplastic material. By the wristband being made of elastic application of the wristband around the user's wrist may be facilitated. Moreover, the elastic properties of the wristband provide for a good feeling around the user's wrist without causing any wear on the wrist. The use of thermoplastic material facilitates the manufacturing of the wristband.

The alarm detection unit may be configured to detect an alarm by detecting simultaneous pressing of the first and second triggering buttons during a predetermined time. By setting a predetermined time for triggering the alarm false alarms may be avoided.

The circuitry further comprises a feedback unit configured to give feedback to the user upon detection of the alarm by the alarm detection unit. By providing feedback upon detection of the alarm the user will get an instant confirmation that he or she has triggered the alarm. This will give the user a safe feeling wearing the alarm triggering device.

The wireless communication unit may be configured to receive a confirmation message from one or more of the one or more alarm receiving units.

The feedback unit may further be configured to give feedback to the user upon receipt of the confirmation message. By providing feedback upon receipt of the confirmation message the user will get an instant confirmation that someone has received the alarm. This will give the user an even more safe feeling wearing the alarm triggering device.

The feedback to the user upon detection of the alarm by the alarm detection unit may be different from the feedback to the user upon receipt of the confirmation message. This will let the user to easily distinguish between the feedback signals.

The feedback unit may comprise one or more of a lighting device for giving visual feedback, a loudspeaker for giving audible feedback or a vibrator for giving tactile feedback. By this different senses of the user may be triggered for the feedback.

The circuitry may further comprise a location determination unit, wherein the location determination unit is configured to determine a location of the user upon triggering of the alarm, and wherein the wireless communication unit is further configured to include the location of the user in the alarm message. Hence, the operator(s) of the alarm receiving unit(s) will in an easy and safe way receive information pertaining to the location of the user of the alarm triggering device. Especially, the location when an alarm is triggered. By setting the setting the location determination unit such that it only determine a location of the user upon triggering of the alarm the personal integrity of the user of the alarm triggering device will be preserved.

The wireless communication unit may be configured to send and receive audio via a telecommunication link, wherein the circuitry further comprises a microphone unit configured to record audio to be sent by the wireless communication unit via the telecommunication link; and a loudspeaker unit configured to playback audio received by the wireless communication unit via the telecommunication link. By this communication between the user of the alarm triggering device and operator(s) or the alarm receiving unit(s) are facilitated.

The microphone unit and/or the loudspeaker unit may be configured to be activated upon the alarm detection unit is detecting the alarm. This will save power of the power source of the alarm triggering unit. Moreover, by activating the microphone unit and/or the loudspeaker unit upon detecting the alarm the personal integrity of the user of the alarm triggering device will be preserved.

The wireless communication unit may be configured to be activated upon the alarm detection unit is detecting the alarm. This will save the power of the power source of the alarm triggering unit. Moreover, by activating the wireless communication unit upon detecting the alarm the personal integrity of the user of the alarm triggering device will be preserved.

The circuitry may further comprise a fall detection unit configured to detect a fall of the user and to emit a fall alarm signal, wherein the alarm detection unit is further configured to detect the alarm by receiving the fall alarm signal.

The power source may be a rechargeable battery, wherein the circuitry further comprises an induction charging unit for charging the power source. The lifetime of the electronic module may hence be prolonged. Moreover, troublesome exchanges of the power source will be avoided. Furthermore, by providing induction charging of the power source no physical connections to the alarm triggering device are needed. This will reduce the attraction of dust and dirt to the alarm triggering device. Moreover, this will make it easier to make the alarm triggering device water proof.

According to a second aspect circuitry for an alarm triggering device is provided. The circuitry comprises a power source configured to power one or more units of the circuitry; first and second triggering buttons; an alarm detection unit configured to detect an alarm by detecting simultaneous actuation of the first and second triggering buttons; and a wireless communication unit configured to wirelessly send an alarm message comprising the alarm to one or more alarm receiving units.

The circuitry may be configured to be removably inserted into a wristband of the alarm triggering device. Hence, an alarm triggering device being easier to assemble is provided. Moreover, this allow for easy recycling of the wristband and the electronic module.

The above mentioned features of the alarm triggering device, when applicable, apply to this second aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Figure 1:
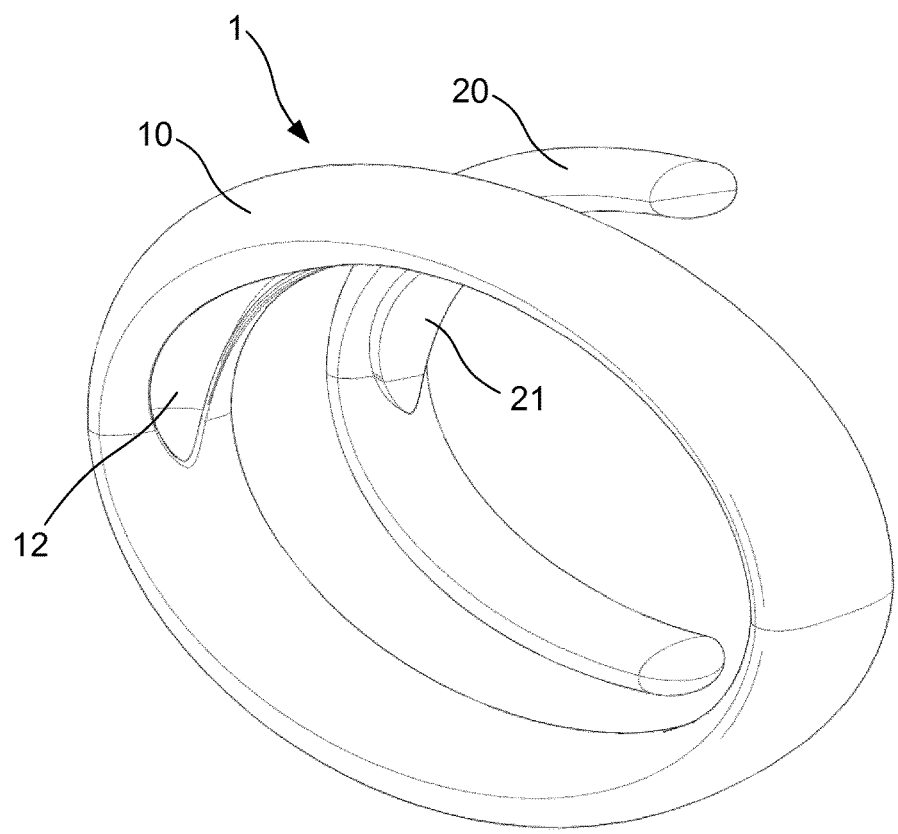
FIG. 1 is schematic side view of a dissembled alarm triggering device comprising a wristband and an electronic module, wherein the electronic module is dissembled from the wristband.

FIG. 1 is schematic side view of an alarm triggering device 1. The alarm triggering device 1 preferably comprises a wristband 10 and an electronic module 20. The electronic module 20 is removably insertable into the wristband 10. In FIG. 1 the alarm triggering device 1 is illustrated in a disassembled state.

The wristband 10 is preferably made of an elastic polymer material. The elastic polymer material is preferably a thermoplastic material. According to a non-limiting example the elastic polymer material may be a silicone-based material. The electronic module 20 comprises a formstable polymer material.

The wristband 10 may comprise an opening 12 for inserting the electronic module 20 therein. Upon inserted into the wristband 10 the electronic module 20 may be removed there-from via the opening 12. The electronic module 20 may comprise a protrusion 21. The protrusion 21 may have a form being complementary to the opening 12 of the wristband 10, and by this a sealing between the wristband and the electronic module may be achieved. Hence, a simple and dean alarm triggering device 1 is provided. The alarm triggering device 1 may hence be worn 24/7 by the user without accumulating dirt thereon.

The electronic module 20 may have a boomerang shape. Hence, the electronic module 20 may be in the form of a circle segment. Hence, the electronic module 20 will follow the shape of the wrist of the user. The ends of the circle segment may be rounded. This will facilitate insertion of the electronic module 20 into the wristband 10.

Figure 2:
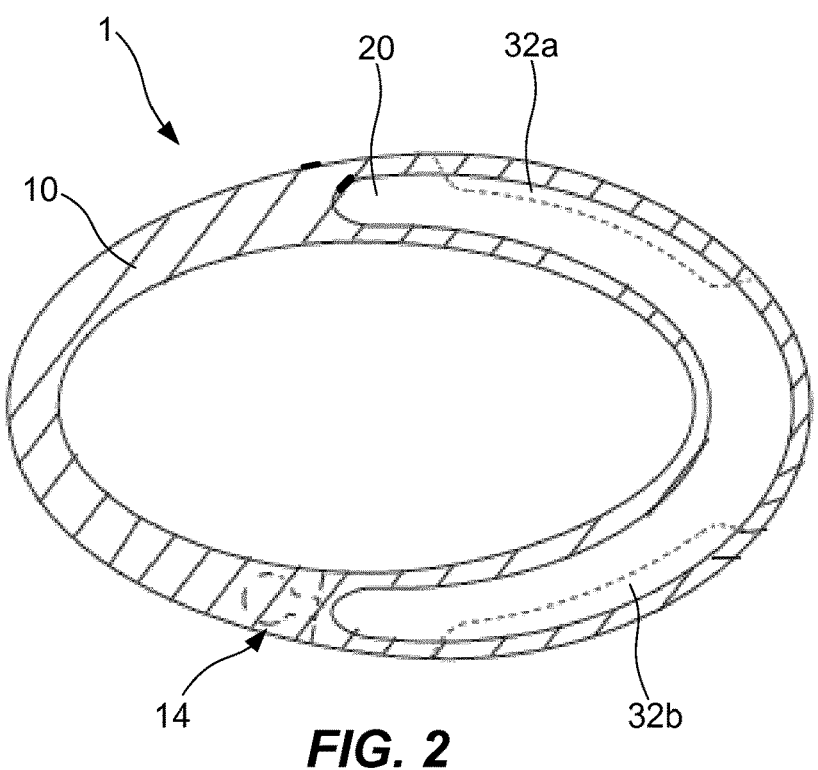
FIG. 2 is a cross sectional view of an assembled alarm triggering device.

FIG. 2 is a cross sectional view of an assembled alarm triggering device 1. Hence, the electronic module 20 is inserted into the wristband 10. The wristband 10 may comprise a locking mechanism 14 for securing two ends of the wristband to each other for forming the wristband. The locking mechanism 14 may be embodied in many different ways known to a person skilled in the art.

During use of the alarm triggering device 1, the wristband 10, with the therein inserted electronic module 20, is preferably worn around a wrist of a user of the alarm triggering device 1.

As illustrated in FIG. 2 the alarm triggering device 1 comprises first and second triggering buttons 32a, 32b. The first and second triggering buttons 32a, 32b are arranged on separate locations along a circumferential extension of the wristband 10. The first and second triggering buttons 32a, 32b allow for simultaneous actuation by the user. The simultaneous actuation is made by applying a gripping force on the first and second triggering buttons 32a, 32b, simultaneously. The gripping force is applied by the user gripping the wristband with one hand. Needless to say, the gripping force is applied by the other hand than the one at which the wristband is worn by the user. Hence, the first triggering button 32a may be arranged to be actuated by applying a radially inward directed force. Likewise, the second triggering button 32b may be arranged to be actuated by applying a radially inward directed force. The first triggering buttons 32a may be actuated by overcoming a resilient force. The second triggering button 32b may be configured to be actuated by overcoming a resilient force.

As mentioned above an alarm is triggered by the user of the alarm triggering device 1 by simultaneous actuation of the first and second triggering buttons 32a, 32b. The simultaneous actuation is performed by the user by applying a gripping force by gripping the wristband 10, at thereby the therein comprised first and second triggering buttons 32a, 32b, by one hand. The user is wearing the wristband 10 around a wrist of one hand of the user and gripping the wristband 10 with another hand of the user. By allowing for simultaneous actuation by the user applying a gripping force by gripping the wristband simple, efficient and fail proof means for triggering the alarm is provided. Applying a gripping force is one of the easiest ways off applying a force for human beings, especially for elder and disabled persons.

As also illustrated in FIG. 2, the first triggering button 32a may be arranged opposite the second triggering button 32b along the circumferential extension of the wristband 10. The first triggering button 32a may have an extension along the circumferential extension of the wristband 10 being at least 5% of the total circumferential extension of the wristband 10, preferably 5-40% of the total circumferential extension of the wristband 10. The second triggering button 32a may have an extension along the circumferential extension of the wristband 10 being at least 5% of the total circumferential extension of the wristband 10, preferably 5-10% of the total circumferential extension of the wristband 10.

The wristband 10 may comprise protrusions indicating where the triggering buttons 32a, 32b are located.

Figure 3:
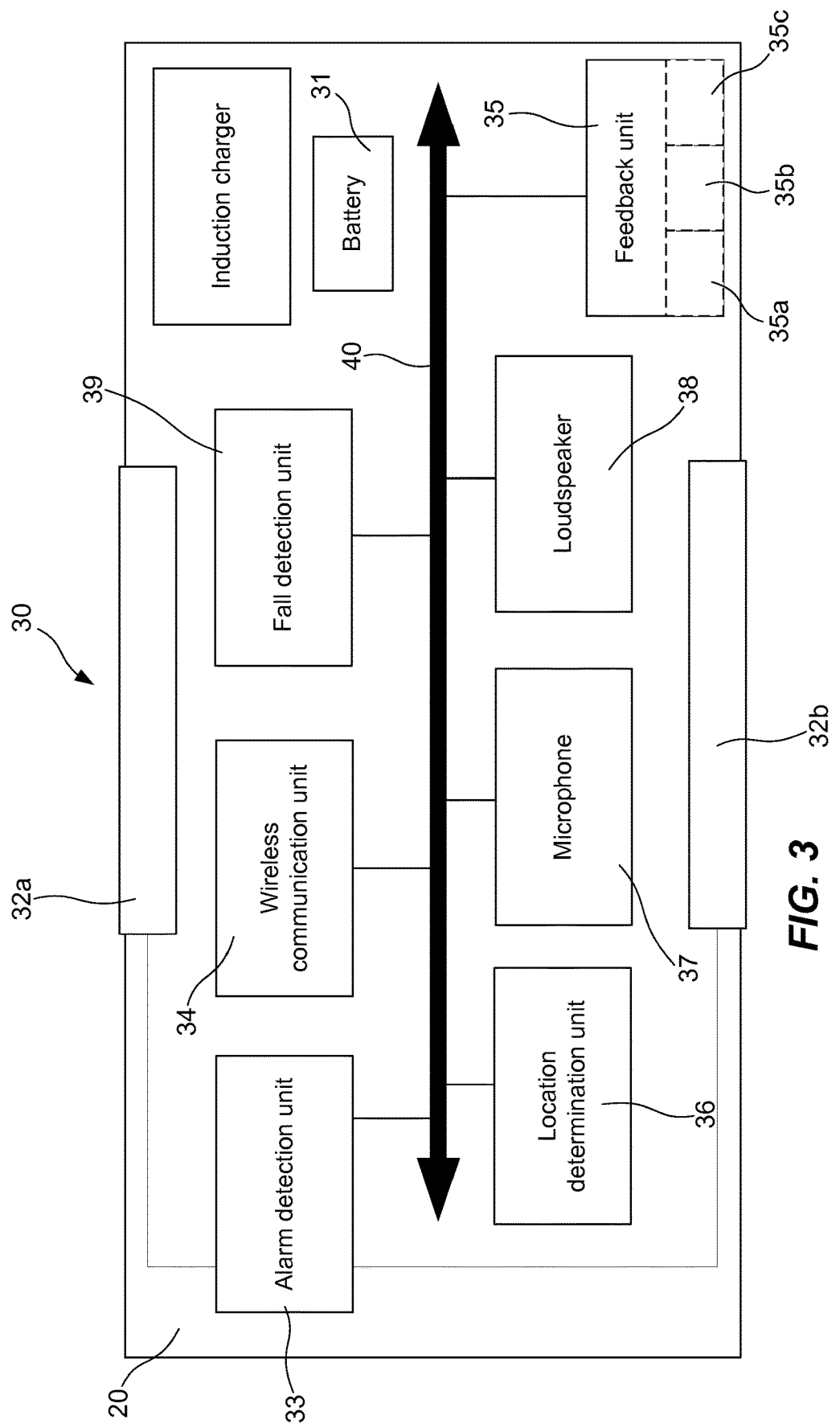
FIG. 3 is a block scheme of a circuitry of the alarm triggering device.

As mentioned above the alarm triggering device 1 comprises first and second triggering buttons 32a, 32b. The first and second triggering buttons 32a, 32b are comprised in a circuitry 30. The circuitry 30 may be comprised in the electronic module 20. In connection with FIG. 3 the circuitry 30 of the alarm triggering device 1 will be discussed. FIG. 3 is a block scheme of the circuitry 30 of the alarm triggering device. In addition to the first and second triggering buttons 32a, 32b, the circuitry comprises an alarm detection unit 33, a wireless communication unit 34 and a power source 31.

The power source 31 is configured to power one or more units of the circuitry 30. With a power source is meant a source being configured to electrical power to the one or more units of the circuitry 30. For example, the power source 31 may be a rechargeable battery. The circuitry 30 may further comprise an induction charging unit 41 for charging the power source 31.

The alarm detection unit 33 is configured to detect an alarm by detecting simultaneous actuation of the first and second triggering buttons 32a, 32b, preferably during a predetermined time. The predetermined time may e.g. be set to time within the interval of 1-10 seconds.

The wireless communication unit 34 is configured to upon detection of the alarm wirelessly send an alarm message to one or more alarm receiving units (not shown). The wireless communication unit 34 may e.g. be a telephone module configured to establish a telephone call with the one or more alarm receiving units. The wireless communication unit 34 may thus comprise a fixed or replaceable SIM-card for configuring the wireless communication unit 34 as a mobile phone unit. The wireless communication unit 34 may be programmable such that the one or more alarm receiving units may be set by the user of the alarm triggering device 1 or be set by a service provider providing the alarm triggering device 1 to the user. The wireless communication unit 34 may further be configured to receive a confirmation message from one or more of the one or more alarm receiving units. Upon receipt of a confirmation message from one or more of the one or more alarm receiving units the wireless communication unit 34 may further be configured to establish a telecommunication link with the one or more of the one or more alarm receiving units. Accordingly, the wireless communication unit 34 may be configured to send and receive audio via the telecommunication link. The wireless communication unit 34 may be configured to be activated upon detection of the alarm by the alarm detection unit 33.

According to one scenario the wireless communication unit 34 is configured to send alarm messages to the one or more alarm receiving units until at least one confirmation message is received.

The wireless communication unit 34 may further be configured to send alarm messages to the one or more alarm receiving units simultaneously.

The wireless communication unit 34 may further be configured to stop sending alarm messages to the other of the one or more alarm receiving units upon receipt of a confirmation message from one of the one or more alarm receiving units.

The circuitry 30 may further comprise a microphone unit 37. The microphone unit 37 is configured to record audio to be sent by the wireless communication unit 34 or to be stored in a memory (not shown) of the circuitry 30. The microphone unit 37 may be configured to be activated upon receipt of the confirmation message. By this the user may communicate with the one or more of the one or more alarm receiving units in connection with the alarm. Alternatively, the microphone unit 37 may be configured to be activated upon triggering of the alarm. In addition to letting the user communicate with the one or more of the one or more alarm receiving units this allow for recording and storing of sounds at the location of the user between the event of triggering the alarm and the receipt of the confirmation message from the one or more of the one or more alarm receiving units.

The circuitry 30 may further comprise a loudspeaker unit 38 configured to playback audio received by the wireless communication unit 34 via the telecommunication link. The loudspeaker unit 38 may be configured to be activated upon receipt of the confirmation message. Alternatively, the loudspeaker unit 38 may be configured to be activated upon the alarm detection unit 33 is detecting the alarm. By either of these alternatives, power of the power source 31 may be saved.

According to one scenario, the user of the alarm triggering device 1 triggers the alarm by gripping the wristband 10 in accordance with the above. This activates the microphone unit 37 and the audio at the location of the user may be recorded. The wireless communication unit 34 is also activated by the alarm and the wireless communication unit 34 sends the alarm message, possibly including the audio recorded at the location of the user, to the one or more alarm receiving units. As mentioned above, upon answering the alarm message the alarm receiving unit sends a confirmation message to the alarm triggering device 1. Upon receipt of the confirmation message or upon triggering the alarm the loudspeaker unit 38 may be activated. Audio may then be sent from the alarm receiving unit directly to the alarm triggering device 1. This will enable the operator of the alarm receiving unit and the user of the alarm triggering device 1 to speak with each over.

The circuitry 30 may further comprise a feedback unit 35. The feedback unit 35 may comprise one or more of a lighting device 35a for giving visual feedback, a loudspeaker 35b for giving audible feedback or a vibrator 35c for giving tactile feedback. According to a non-limiting example the lighting device 35a may comprise LEDs. The wristband 10 may comprise a translucent portion allowing light from the lighting device 35a of the feedback unit 35 escaping there through. The translucent portion of the wristband 10 may be located on a side surface of the wristband 10 and may have an extension along the circumferential extension of the wristband 10. The feedback unit 35 may be configured to give feedback to the user upon detection of the alarm by the alarm detection unit 33. Further, the feedback unit 35 may be configured to give feedback to the user upon receipt of the confirmation message from one or more of the one or more alarm receiving units. Preferably the feedback unit 35 is configured to give different feedback to the user depending on if the feedback is give as a confirmation on activated alarm or if the feedback is give as a confirmation on received confirmation message. As a non-limiting example the lighting device 35a may be set to give feedback emitting light of a first color upon activation of the alarm and to give feedback emitting light of a second color upon receipt of the confirmation message, wherein the second color is different from the first color. The loudspeaker 35b of the feedback unit 35 may be set to emit different sounds depending on the type of feedback and/or the vibrator 35c of the feedback unit 35 may be set to emit different tactile signals depending on the type of feedback. Alternatively or in combination, the feedback pertaining to activation of the alarm and the feedback pertaining to the receipt of the confirmation message may be given by different ones of the lighting device 35a, the loudspeaker 35b and the vibrator 35c.

The circuitry 30 may further comprise a location determination unit 36. According to a no limiting example the location determination unit 36 may be a GPS-unit. The location determination unit 36 is configured to determine a location of the user upon triggering of the alarm. In such case the wireless communication unit 34 may further be configured to include the location of the user in the alarm message. Hence, all of the one or more alarm receiving units may get a position where the user was located when the alarm was triggered. According to one scenario, the user of the alarm triggering device 1 triggers the alarm by gripping the wristband 10 in accordance with the above. This activates the location determination unit 36 which determines the location of the user. The wireless communication unit 34 is also activated by the alarm and the wireless communication unit 34 sends the alarm message, including the location of the user, to the one or more alarm receiving units. Further, the location determination unit 36 may update the location of the user during an active telecommunication link. The wireless communication unit 34 may be configured to send the updated location of the user to the one or more alarm receiving units.

The circuitry 30 may further comprise a communication bus 40. The units 33, 34, 35, 36, 37, 38, 39 of the circuitry 30 may be configured to communicate via the communication bus 40.

One or more of the units 33, 34, 35, 36, 37, 38, 39 of the circuitry 30 may be implemented as dedicated hardware components. One or more of the units 33, 34, 35, 36, 37, 38, 39 of the circuitry 30 may be implemented as digital software components being run on a data processing unit. The circuitry 30 may hence comprise a processing unit. The circuitry 30 may further comprise a non-transitory computer readable digital storage medium for storing the above mentioned one or more digital software components.

The person skilled in the art realizes that the present invention by no means is limited to the preferred embodiments described above. On the contrary, many modifications and variations are possible within the scope of the appended claims.

For example, above the alarm triggering device 1 has been exemplified as a device comprising the wristband 10 and the electronic module 20 removably insertable into the wristband 10. However, according to embodiments the alarm triggering device 1 may be formed by molding the wristband 10 around the circuitry 30. Hence, the circuitry 30 may be encapsulated within the wristband 10. According to yet other embodiments, the alarm triggering device 1 may be formed by molding the wristband 10 around the electronic module 20, and the therein comprised circuitry 30. Hence, the electronic module 20, and the therein comprised circuitry 30, may be encapsulated within the wristband 10.

Moreover, the circuitry 30 may comprise a fall detection unit 39. The fall detection unit 39 is configured to detect a fall of the user. Upon detection of a fall of the user the fall detection unit 39 is configured to emit a fall alarm signal. The alarm detection unit 33 is in such case further configured to detect the alarm by receiving the fall alarm signal. The fall detection unit 39 may be implemented in various ways known to a person skilled in the art. A non-limiting example is a fall detection unit 39 based on an accelerometer.

Additionally, variations to the disclosed embodiments can be understood and effected by the skilled person in practicing the claimed invention, from a study of the drawings, the disclosure, and the appended claims.

The invention claimed is:

1. An alarm triggering device comprising:
    a wristband wearable by a user; and
    circuitry comprising:
        a power source configured to power one or more units of the circuitry;
        first and second triggering buttons arranged on separate locations along a circumferential extension of the wristband allowing for simultaneous actuation by the user applying a gripping force by gripping the wristband;
        an alarm detection unit configured to detect an alarm by detecting simultaneous actuation of the first and second triggering buttons;
        a wireless communication unit configured to upon detection of the alarm wirelessly send an alarm message to one or more alarm receiving units and to receive a confirmation message from one or more of the one or more alarm receiving units; and
        a feedback unit configured to give feedback to the user upon detection of the alarm by the alarm detection unit to thereby provide the user with a first safety assurance, and to give feedback to the user upon receipt of the confirmation message to thereby provide the user with a second safety assurance, wherein the feedback to the user upon detection of the alarm by the alarm detection unit is different from the feedback to the user upon receipt of the confirmation message.

2. The alarm triggering device according to claim 1, wherein the first and second triggering buttons are configured to be actuated by overcoming a resilient force.

3. The alarm triggering device according to claim 1, wherein the first button is arranged opposite the second button along the circumferential extension of the wristband.

4. The alarm triggering device according to claim 1, wherein the first button is arranged to be actuated by applying a radially inward directed force and wherein the second button is arranged to be actuated by applying a radially inward directed force.

5. The alarm triggering device according to claim 1, wherein the power source, the alarm detection unit and the wireless communication unit are comprised in an electronic module removably integrated with the wristband.

6. The alarm triggering device according to claim 5, wherein the electronic module is made of formstable polymer material, preferably thermoplastic material.

7. The alarm triggering device according to claim 1, wherein the wristband is made of elastic polymer material, preferably thermoplastic material.

8. The alarm triggering device according to claim 1, wherein the alarm detection unit is configured to detect an alarm by detecting simultaneous pressing of the first and second triggering buttons during a predetermined time.

9. The alarm triggering device according claim 1, wherein the feedback unit comprises one or more of a lighting device for giving visual feedback, a loudspeaker for giving audible feedback or a vibrator for giving tactile feedback.

10. The alarm triggering device according to claim 1, wherein the circuitry further comprises a location determination unit, wherein the location determination unit is configured to determine a location of the user upon triggering of the alarm, and wherein the wireless communication unit is further configured to include the location of the user in the alarm message.

11. The alarm triggering device according to claim 1, wherein the wireless communication unit is configured to send and receive audio via a telecommunication link, wherein the circuitry further comprises a microphone unit configured to record audio to be sent by the wireless communication unit via the telecommunication link; and a loudspeaker unit configured to playback audio received by the wireless communication unit via the telecommunication link.

12. The alarm triggering device according to claim 11, wherein the microphone unit and/or the loudspeaker unit is configured to be activated upon the alarm detection unit is detecting the alarm.

13. The alarm triggering device according to claim 1, wherein the wireless communication unit is configured to be activated upon the alarm detection unit is detecting the alarm.

14. The alarm triggering device according to claim 1, wherein the circuitry further comprises a fall detection unit configured to detect a fall of the user and to emit a fall alarm signal, wherein the alarm detection unit is further configured to detect the alarm by receiving the fall alarm signal.

15. The alarm triggering device according to claim 1, wherein the power source is a rechargeable battery, and wherein the circuitry further comprises an induction charging unit for charging the power source.

16. The alarm triggering device of claim 1, wherein the feedback to the user upon detection of the alarm by the alarm detection unit user is selected from one of a visual feedback, audible feedback, or a tactile feedback, and wherein the feedback to the user upon receipt of the confirmation message is selected from a different one of the visual feedback, audible feedback, or a tactile feedback.

17. Circuitry for an alarm triggering device, the circuitry comprising:
    a power source configured to power one or more units of the circuitry;
    first and second triggering buttons;
    an alarm detection unit configured to detect an alarm by detecting simultaneous actuation of the first and second triggering buttons; and
    a wireless communication unit configured to wirelessly send an alarm message comprising the alarm to one or more alarm receiving units and to receive a confirmation message from one or more of the one or more alarm receiving units; and
    a feedback unit configured to give feedback to the user upon detection of the alarm by the alarm detection unit to thereby provide the user with a first safety assurance and to give feedback to the user upon receipt of the confirmation message to thereby provide the user with a second safety assurance, wherein the feedback to the user upon detection of the alarm by the alarm detection unit is different from the feedback to the user upon receipt of the confirmation message.

18. The circuitry according to claim 17, wherein the circuitry is configured to be removably inserted into a wristband of the alarm triggering device.

19. The alarm triggering device of claim 17, wherein the feedback to the user upon detection of the alarm by the alarm detection unit user is selected from one of a visual feedback, audible feedback, or a tactile feedback, and wherein the feedback to the user upon receipt of the confirmation message is selected from a different one of the visual feedback, audible feedback, or a tactile feedback.

20. An alarm triggering device comprising:
   a wristband wearable by a user, the wristband is made of elastic polymer material; and
   an electronic module comprising a circuitry comprising:
      a power source configured to power one or more units of the circuitry;
      first and second triggering buttons arranged on separate locations along a circumferential extension of the wristband allowing for simultaneous actuation by the user applying a gripping force by gripping the wristband;
      an alarm detection unit configured to detect an alarm by detecting simultaneous actuation of the first and second triggering buttons;
      a wireless communication unit configured to upon detection of the alarm wirelessly send an alarm message to one or more alarm receiving units; and
      a feedback unit configured to provide the user with first and second safety assurances relating respectively to detection of the alarm by the alarm detection unit and confirmation of receipt of the alarm by one of the one or more alarm receiving units,
   wherein the electronic module is configured to be removably inserted into the wristband,
   wherein the wristband comprises an opening on an inside of the wristband for inserting the electronic module therein.

21. The alarm triggering device according to claim 20, wherein the electronic module is in the form of a circle segment.

22. The alarm triggering device according to claim 20, wherein the electronic module comprises a protrusion having a form being complementary to the opening of the wristband.

23. The alarm triggering device of claim 20, wherein the first safety assurance comprises feedback selected from one of a visual feedback, audible feedback, or a tactile feedback, and the second safety assurance comprises feedback selected from a different one of the visual feedback, audible feedback, or a tactile feedback.

* * * * *